United States Patent
Spraker et al.

(10) Patent No.: US 7,536,225 B2
(45) Date of Patent: May 19, 2009

(54) ENDO-PELVIC FASCIA PENETRATING HEATING SYSTEMS AND METHODS FOR INCONTINENCE TREATMENT

(75) Inventors: Terry E. Spraker, Portola Valley, CA (US); Edward Luttich, Dublin, CA (US)

(73) Assignee: AMS Research Corporation, Minnetonka, MN (US)

(*) Notice: Subject to any disclaimer, the term of this patent is extended or adjusted under 35 U.S.C. 154(b) by 646 days.

(21) Appl. No.: 11/040,815

(22) Filed: Jan. 21, 2005

(65) Prior Publication Data
US 2006/0167533 A1 Jul. 27, 2006

(51) Int. Cl.
*A61F 7/12* (2006.01)
(52) U.S. Cl. .................. 607/101; 607/96; 607/102
(58) Field of Classification Search ........... 607/96–106, 607/113
See application file for complete search history.

(56) References Cited

U.S. PATENT DOCUMENTS

| | | | |
|---|---|---|---|
| 373,399 A | 11/1887 | Hamilton |
| 728,883 A | 5/1903 | Downes |
| 3,575,158 A | 4/1971 | Summers |
| 3,749,098 A | 7/1973 | De Bennetot |
| 3,924,631 A | 12/1975 | Mancusi, Jr. |
| 3,926,175 A | 12/1975 | Allen et al. |
| 3,934,589 A | 1/1976 | Zimmer |
| 3,939,821 A | 2/1976 | Roth |
| 4,311,145 A | 1/1982 | Esty et al. |
| 4,326,529 A | 4/1982 | Doss et al. |
| 4,381,007 A | 4/1983 | Doss |
| 4,409,453 A | 10/1983 | Smith |
| 4,453,536 A | 6/1984 | Abild |
| 4,679,561 A | 7/1987 | Doss |
| 4,686,962 A | 8/1987 | Haber |
| 4,765,331 A | 8/1988 | Petruzzi et al. |
| 4,773,393 A | 9/1988 | Haber et al. |
| 4,776,344 A | 10/1988 | Shirasaki et al. |

(Continued)

FOREIGN PATENT DOCUMENTS

WO WO 93/07815 A1 4/1993

(Continued)

OTHER PUBLICATIONS

U.S. Appl. No. 60/022,790, filed Jul. 20, 1996, Baker.

(Continued)

*Primary Examiner*—Roy D Gibson
(74) *Attorney, Agent, or Firm*—Oppenheimer Wolff & Donnelly LLP; Adam P. Kiedrowski

(57) ABSTRACT

Retrograde methods of accessing and treating collagenous pelvic tissue from a fixed point behind the endo-pelvic fascia, particularly from a space of retzius, are disclosed. Performing treatment from the space of retzius provides for simple and reliable placement and application of the system which in turn enhances both safety and efficacy of such retrograde methodologies. Generally, the systems of the present invention comprise at least a two-part assembly including a penetrating cannula or trocar and an expansible energy applying applicator that is preferably dismounted from behind the endo-pelvic fascia, particularly the space of retzius. The systems and methods are particularly well suited for the treatment of incontinence and other conditions related to insufficient collagenous pelvic tissue support.

49 Claims, 8 Drawing Sheets

U.S. PATENT DOCUMENTS

| | | |
|---|---|---|
| 4,802,479 A | 2/1989 | Haber et al. |
| 4,807,620 A | 2/1989 | Strul et al. |
| 4,832,680 A | 5/1989 | Haber et al. |
| 4,976,709 A | 12/1990 | Sand |
| 4,994,019 A | 2/1991 | Fernandez et al. |
| 5,003,991 A | 4/1991 | Takayama et al. |
| 5,012,822 A | 5/1991 | Schwarz |
| 5,035,696 A | 7/1991 | Rydell |
| 5,041,109 A | 8/1991 | Abela |
| 5,056,531 A | 10/1991 | Shimoyama |
| 5,057,106 A | 10/1991 | Kasevich et al. |
| 5,098,429 A | 3/1992 | Sterzer |
| 5,100,423 A * | 3/1992 | Fearnot ............ 606/159 |
| 5,103,804 A | 4/1992 | Abele et al. |
| 5,140,999 A | 8/1992 | Ardito |
| 5,190,517 A | 3/1993 | Zieve et al. |
| 5,201,732 A | 4/1993 | Parins et al. |
| 5,213,097 A | 5/1993 | Zeindler |
| 5,230,334 A | 7/1993 | Klopotek |
| 5,234,409 A | 8/1993 | Goldberg et al. |
| 5,256,133 A | 10/1993 | Spitz |
| 5,281,217 A | 1/1994 | Edwards et al. |
| 5,281,218 A | 1/1994 | Imran |
| 5,282,799 A | 2/1994 | Rydell |
| 5,293,869 A | 3/1994 | Edwards et al. |
| 5,304,123 A | 4/1994 | Atala et al. |
| 5,309,910 A | 5/1994 | Edwards et al. |
| 5,314,465 A | 5/1994 | Maurer et al. |
| 5,314,466 A | 5/1994 | Stern et al. |
| 5,330,518 A | 7/1994 | Neilson et al. |
| 5,348,554 A | 9/1994 | Imran et al. |
| 5,366,490 A | 11/1994 | Edwards et al. |
| 5,370,671 A | 12/1994 | Maurer et al. |
| 5,370,675 A | 12/1994 | Edwards et al. |
| 5,370,677 A | 12/1994 | Rudie et al. |
| 5,370,678 A | 12/1994 | Edwards et al. |
| 5,376,064 A | 12/1994 | Cerny |
| 5,385,544 A | 1/1995 | Edwards et al. |
| 5,403,312 A | 4/1995 | Yates et al. |
| 5,405,346 A | 4/1995 | Grundy et al. |
| 5,411,475 A | 5/1995 | Atala et al. |
| 5,415,666 A | 5/1995 | Gourlay et al. |
| 5,417,208 A | 5/1995 | Winkler |
| 5,423,811 A | 6/1995 | Imran et al. |
| 5,431,649 A | 7/1995 | Mulier et al. |
| 5,437,603 A | 8/1995 | Cerny et al. |
| 5,437,664 A | 8/1995 | Cohen et al. |
| 5,443,470 A | 8/1995 | Stern et al. |
| 5,447,529 A | 9/1995 | Marchlinski et al. |
| 5,454,809 A | 10/1995 | Janssen |
| 5,458,596 A | 10/1995 | Lax et al. |
| 5,462,545 A | 10/1995 | Wang et al. |
| 5,480,417 A | 1/1996 | Hascoet et al. |
| 5,496,312 A | 3/1996 | Klicek |
| 5,505,730 A | 4/1996 | Edwards |
| 5,514,130 A | 5/1996 | Baker |
| 5,514,155 A | 5/1996 | Daneshvar |
| 5,516,396 A | 5/1996 | Maurer et al. |
| 5,520,684 A | 5/1996 | Imran |
| 5,533,999 A | 7/1996 | Hood et al. |
| 5,536,267 A | 7/1996 | Edwards et al. |
| 5,540,655 A | 7/1996 | Edwards et al. |
| 5,540,679 A | 7/1996 | Fram et al. |
| 5,542,916 A | 8/1996 | Hirsch et al. |
| 5,545,137 A | 8/1996 | Rudie et al. |
| 5,549,644 A | 8/1996 | Lundquist et al. |
| 5,554,110 A | 9/1996 | Edwards et al. |
| 5,556,396 A | 9/1996 | Cohen et al. |
| 5,558,672 A | 9/1996 | Edwards et al. |
| 5,569,241 A | 10/1996 | Edwards |
| 5,569,242 A | 10/1996 | Lax et al. |
| 5,575,788 A | 11/1996 | Baker et al. |
| 5,578,052 A | 11/1996 | Koros et al. |
| 5,588,960 A | 12/1996 | Edwards et al. |
| 5,591,125 A | 1/1997 | Edwards et al. |
| 5,609,598 A | 3/1997 | Laufer et al. |
| 5,611,515 A | 3/1997 | Benderev et al. |
| 5,628,770 A | 5/1997 | Thome et al. |
| 5,649,973 A | 7/1997 | Tierney et al. |
| 5,660,836 A | 8/1997 | Knowlton |
| 5,667,488 A | 9/1997 | Lundquist et al. |
| 5,673,695 A | 10/1997 | McGee et al. |
| 5,687,723 A | 11/1997 | Avitall |
| 5,688,267 A | 11/1997 | Panescu et al. |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,707,367 A | 1/1998 | Nilsson |
| 5,716,385 A | 2/1998 | Mittal et al. |
| 5,728,119 A | 3/1998 | Smith et al. |
| 5,746,224 A | 5/1998 | Edwards |
| 5,755,753 A | 5/1998 | Knowlton |
| 5,769,879 A | 6/1998 | Richards et al. |
| 5,769,880 A | 6/1998 | Truckai et al. |
| 5,792,140 A | 8/1998 | Tu et al. |
| 5,807,395 A | 9/1998 | Mulier et al. |
| 5,810,847 A | 9/1998 | Laufer et al. |
| 5,836,874 A | 11/1998 | Swanson et al. |
| 5,843,077 A | 12/1998 | Edwards |
| 5,871,524 A | 2/1999 | Knowlton |
| 5,879,348 A | 3/1999 | Owens et al. |
| 5,895,417 A | 4/1999 | Pomeranz et al. |
| 5,899,897 A | 5/1999 | Rabin et al. |
| 5,919,219 A | 7/1999 | Knowlton |
| 5,948,011 A | 9/1999 | Knowlton |
| 5,954,720 A | 9/1999 | Wilson et al. |
| 5,957,920 A | 9/1999 | Baker |
| 5,957,961 A | 9/1999 | Maguire et al. |
| 5,964,755 A | 10/1999 | Edwards |
| 6,009,877 A | 1/2000 | Edwards |
| 6,015,406 A | 1/2000 | Goble et al. |
| 6,015,407 A | 1/2000 | Rieb et al. |
| 6,035,238 A | 3/2000 | Ingle et al. |
| 6,044,846 A | 4/2000 | Edwards |
| 6,044,847 A | 4/2000 | Carter et al. |
| 6,047,700 A | 4/2000 | Eggers et al. |
| 6,056,744 A | 5/2000 | Edwards |
| 6,068,628 A | 5/2000 | Fanton et al. |
| 6,073,052 A | 6/2000 | Zelickson et al. |
| 6,080,125 A | 6/2000 | Mott |
| 6,081,749 A | 6/2000 | Ingle et al. |
| 6,091,993 A | 7/2000 | Bouchier et al. |
| 6,091,995 A | 7/2000 | Ingle et al. |
| 6,104,959 A | 8/2000 | Spertell |
| 6,105,581 A | 8/2000 | Eggers et al. |
| 6,139,569 A | 10/2000 | Ingle et al. |
| 6,156,060 A | 12/2000 | Roy et al. |
| 6,169,926 B1 | 1/2001 | Baker |
| 6,197,022 B1 | 3/2001 | Baker |
| 6,216,704 B1 | 4/2001 | Ingle et al. |
| 6,228,078 B1 | 5/2001 | Eggers et al. |
| 6,238,891 B1 | 5/2001 | Ingle et al. |
| 6,241,753 B1 | 6/2001 | Knowlton |
| 6,273,886 B1 | 8/2001 | Edwards et al. |
| 6,277,116 B1 | 8/2001 | Utely et al. |
| 6,283,961 B1 | 9/2001 | Underwood et al. |
| 6,283,987 B1 | 9/2001 | Laird et al. |
| 6,290,699 B1 | 9/2001 | Hall et al. |
| 6,292,700 B1 | 9/2001 | Morrison et al. |
| 6,322,584 B2 | 11/2001 | Ingle et al. |
| 6,334,074 B1 | 12/2001 | Spertell |
| 6,346,111 B1 | 2/2002 | Gordon et al. |
| 6,413,253 B1 | 7/2002 | Koop et al. |

| | | | |
|---|---|---|---|
| 6,416,504 B2 | 7/2002 | Mosel et al. | |
| 6,425,853 B1 | 7/2002 | Edwards | |
| 6,425,877 B1 | 7/2002 | Edwards | |
| 6,428,538 B1 | 8/2002 | Blewett et al. | |
| 6,463,331 B1 | 10/2002 | Edwards | |
| 6,470,219 B1 | 10/2002 | Edwards et al. | |
| 6,544,260 B1 | 4/2003 | Markel et al. | |
| 6,546,934 B1 | 4/2003 | Ingle et al. | |
| 6,558,381 B2 | 5/2003 | Ingle et al. | |
| 6,572,639 B1 | 6/2003 | Ingle et al. | |
| 6,587,731 B1 * | 7/2003 | Ingle et al. | 607/101 |
| 6,685,623 B2 | 2/2004 | Presthus et al. | |
| 6,692,490 B1 | 2/2004 | Edwards | |
| 6,751,507 B2 | 6/2004 | Morrison et al. | |
| 6,776,779 B1 | 8/2004 | Roy et al. | |
| 2001/0018606 A1 | 8/2001 | Ingle et al. | |
| 2003/0036804 A1 | 2/2003 | Thomas et al. | |
| 2003/0159700 A1 * | 8/2003 | Laufer et al. | 128/898 |
| 2003/0181897 A1 | 9/2003 | Thomas et al. | |
| 2004/0193238 A1 | 9/2004 | Mosher et al. | |
| 2005/0165439 A1 * | 7/2005 | Weber et al. | 606/191 |

FOREIGN PATENT DOCUMENTS

| | | |
|---|---|---|
| WO | WO 93/15664 A1 | 8/1993 |
| WO | WO 96/00041 A1 | 1/1996 |
| WO | WO 96/00042 A1 | 1/1996 |
| WO | WO 96/34568 A1 | 11/1996 |
| WO | WO 97/15237 A1 | 5/1997 |
| WO | WO 97/15238 A1 | 5/1997 |
| WO | WO 97/20510 A1 | 6/1997 |
| WO | WO 97/24992 A1 | 7/1997 |
| WO | WO 97/32532 A1 | 9/1997 |
| WO | WO 97/39688 A2 | 10/1997 |
| WO | WO 97/43970 A1 | 11/1997 |
| WO | WO 97/43971 A2 | 11/1997 |
| WO | WO 98/05286 A1 | 2/1998 |
| WO | WO 98/05380 A1 | 2/1998 |
| WO | WO 98/07468 A1 | 2/1998 |
| WO | WO 98/19613 A1 | 5/1998 |
| WO | WO 98/38936 A1 | 9/1998 |
| WO | WO 99/16502 A1 | 4/1999 |
| WO | WO 99/17690 A1 | 4/1999 |
| WO | WO 00/06047 A1 | 2/2000 |
| WO | WO 01/22897 A1 | 4/2001 |

OTHER PUBLICATIONS

U.S. Appl. No. 60/024,974, filed Aug. 30, 1996, Baker.

Benson, Thomas J., *Female Pelvic Floor Disorders: Investigation and Management* Norton Medical Books, W.W. Norton & Company, New York, New York, 1992, pp. 239-240.

Finger, Paul T. et al., "Heat Shrinkage of Extraocular Muscle Tendon," *Arch. Ophthalmol.*, vol. 105, May 1987, pp. 716-718.

Fulmer et al., "Acute and Long-Term Outcomes of Radio Frequency Bladder Neck Suspension," *The Journal of Urology*, vol. 167, 141-145, Jan. 2002.

Hayes et al., "Prediction of Transient Temperature Fields and Cumulative Tissue Destruction for Radio Frequency Heating of a Tumor," Medical Physics, University of Texas, Austin, Texas; 12(6):1985.

Kursch, M.D., Elroy D. et al., *Female Urology*, J.B. Lippincott Company, Philadelphia, Pennsylvania, 1994, pp. 3-16 and 285-298.

Raz, Shlomo, *Female Urology, Second Edition*, W.B. Saunders Company, Philadelphia, Pennsylvania, 1996, pp. 57-72, 126, 319-357, and 445-456.

* cited by examiner

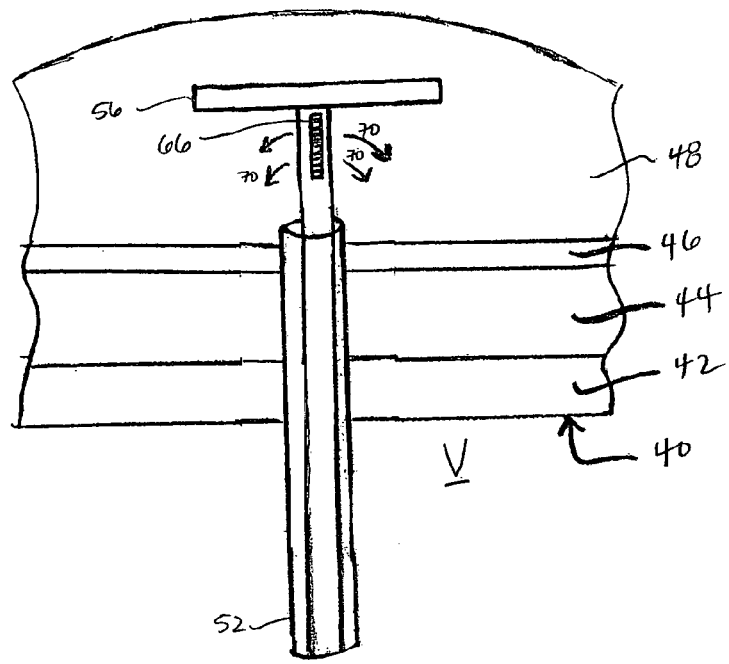
FIG. 6C
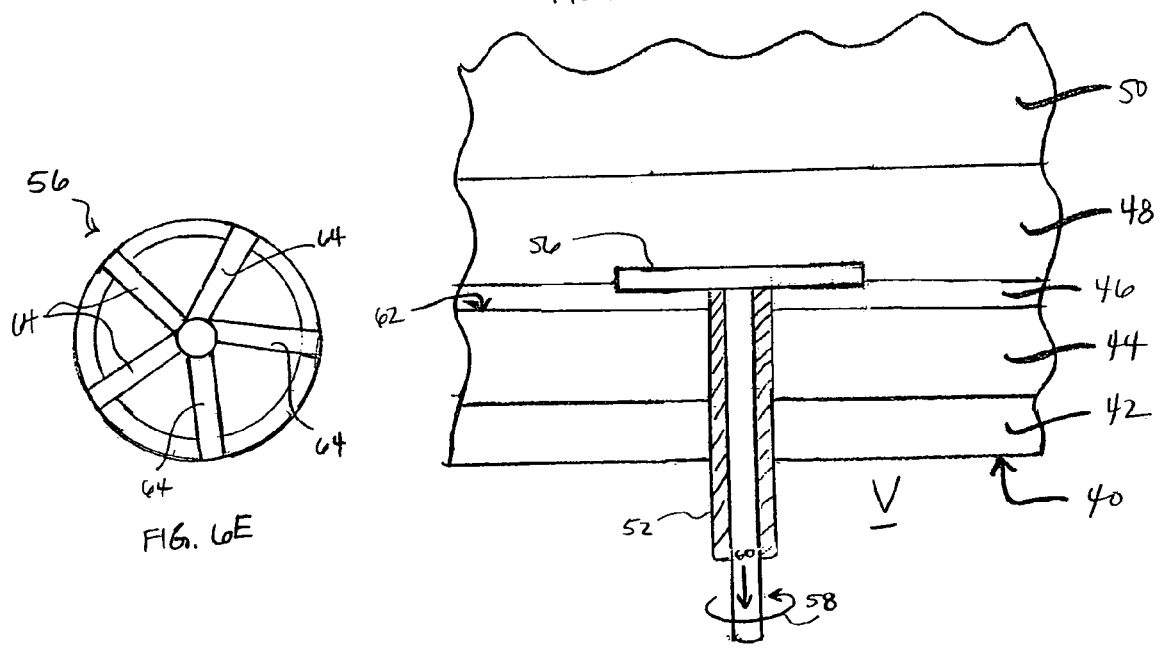
FIG. 6E
FIG. 6D

ENDO-PELVIC FASCIA PENETRATING HEATING SYSTEMS AND METHODS FOR INCONTINENCE TREATMENT

BACKGROUND OF THE INVENTION

The present invention generally relates to medical systems and methods, particularly for the treatment of urinary incontinence.

Urinary incontinence arises in both men and women with varying degrees of severity, and from different causes. In men, the condition frequently occurs as a result of prostatectomies which result in mechanical damage to the urinary sphincter. In women, the condition typically arises after pregnancy when musculoskeletal damage has occurred as a result of inelastic stretching of the structures supporting the genitourinary tract. Specifically, pregnancy can result in inelastic stretching of the pelvic floor, the external sphincter, and the tissue structures which support the bladder, urethra, and bladder neck region. In each of these cases, urinary leakage typically occurs when a patient's abdominal pressure increases as a result of stress, e.g., coughing, sneezing, laughing, exercise, or the like.

Treatment of urinary incontinence can take a variety of forms. Most simply, the patient can wear absorptive devices or clothing, which is often sufficient for minor leakage events. Alternatively or additionally, patients may undertake exercises intended to strengthen the muscles in the pelvic region, or may attempt a behavior modification intended to reduce the incidence of urinary leakage.

In cases where such non-interventional approaches are inadequate or unacceptable, the patient may undergo surgery to correct the problem. A wide variety of procedures have been developed to correct urinary incontinence in women. Several of these procedures are specifically intended to support the bladder neck region. For example, sutures, straps or other artificial structures are often looped around the bladder neck and affixed to the pelvis, the endo-pelvic fascia, the ligaments which support the bladder, or the like. Other procedures involve surgical injections of bulking agents, inflatable balloons, or other elements to mechanically support the bladder neck.

In work done related to the present invention, it has been proposed to treat urinary incontinence by selectively remodeling a portion of the pelvic support tissue, often so as to reposition the bladder and/or urogenital tract. U.S. Pat. No. 6,091,995 generally describes laparoscopic and other minimally invasive devices, methods, and systems for shrinking tissues, particularly for treatment of incontinence. U.S. Pat. Nos. 6,216,704; 6,558,381; and 6,546,934, describe noninvasive devices, methods, and systems for shrinking of tissues, often by cooling a surface of an intermediate tissue and directing energy through the cooled intermediate tissue to the target tissue so as to effect shrinkage. U.S. Pat. Nos. 6,156,060; 6,572,639; and 6,776,779, are directed to static devices and methods to shrink tissues for incontinence. Finally, U.S. Pat. No. 6,292,700 describes an endo-pelvic fascia treatment for incontinence in which a strength of a collagenous tissue increases, optionally without collagenous tissue contraction. U.S. patent application Ser. No. 10/759,732 describes non-surgical incontinence treatment systems and methods. Each of these patents is assigned to the assignee of the present application, and their full disclosures are incorporated herein by reference.

While these recent proposals for treatment of incontinence represent significant advancements in the art, alternative systems and methods for the treatment of incontinence and other conditions related to insufficient collagenous pelvic tissue support could be advantageous.

BRIEF SUMMARY OF THE INVENTION

The present invention provides systems and methods for the treatment of incontinence and other conditions related to insufficient collagenous pelvic tissue support. In particular, retrograde methods of accessing and treating the collagenous pelvic tissue from a fixed point behind the endo-pelvic fascia, particularly from a space of retzius, are provided. Performing the treatment from the space of retzius provides for simple and reliable placement and application of the system which in turn enhances both safety and efficacy of such retrograde methodologies. The present invention has particular application in the treatment of incontinence, such as female urinary stress incontinence, and other conditions related to insufficient collagenous pelvic tissue support, such as bladder neck descent. Generally, the systems of the present invention comprise at least a two-part assembly including a penetrating cannula or trocar and an expansible energy applying applicator that is preferably dismounted from behind the endo-pelvic fascia, particularly the space of retzius.

In a first aspect of the present invention, a method for heating support tissue of a patient comprises deploying an expansible electrode apparatus at a fixed point behind collagenous endo-pelvic fascia. Energy is then applied to heat the endo-pelvic fascia. As described above, preferably the apparatus is deployed in the space of retzius. Heating the endo-pelvic fascia treats conditions such as urinary stress incontinence, bladder neck descent, and the like by shrinking and/or stiffening the endo-pelvic support tissue to reposition and/or raise the urinary bladder. It will be appreciated that there are a number of energy modalities to heat, shrink, and/or stiffen the endo-pelvic fascia which supports at least a portion of patient's bladder, urethra, or bladder neck. Preferably, radio frequency (RF) power is used to project energy into the endo-pelvic fascia in a monopolar or bipolar operation depending on how a power supply is configured. Optionally, the energy applying applicator may project microwave energy from the space of retzius directly through a fat layer tissue structure and into a back surface of the target endo-pelvic tissue. Still further, the applied energy may comprise ultrasound energy, laser energy, passive-resistive heating, infrared, or the like.

The methods of the present invention further comprise positioning a cannula or sheath in conjunction with an introducer (e.g., scalpel, needle, etc.) or a sharpened trocar tube within a patient's vagina and penetrating a distal end of the cannula through the collagenous endo-pelvic fascia and behind the endo-pelvic fascia prior to deploying the apparatus. Penetrating may comprise advancing the cannula through vaginal mucosa, endo-pelvic fascia, and a fat layer tissue structure. In particular, penetrating may comprise advancing the introducer through the collagenous endo-pelvic fascia, sliding the cannula over the introducer, and removing the introducer while the cannula is positioned behind the endo-pelvic fascia. Preferably, penetrating comprises positioning the cannula in the space of retzius or in a fat layer tissue structure surrounding a back surface of the endo-pelvic fascia. The penetrating cannula advantageously allows for proper navigation and application of the apparatus from behind the endo-pelvic fascia, particularly in tissue planes that are difficult to access. For example, cannula penetration may facilitate access to the desired areas in women with small anatomical structures. Additionally, cannula penetration provides a non-surgical incisionless treatment which may obviate the need for abdominal puncture sites or stitches to the vaginal wall or mucosa.

In one embodiment, deploying may comprise inserting the expansible electrode apparatus through the cannula until a distal end of the apparatus is expanded in the space of retzius. In such an embodiment, the self-expansible apparatus is expanded simply by release from the constraining cannula or sheath surrounding the apparatus. Once the apparatus is in the expanded configuration, the apparatus is pulled in a proximal direction toward the endo-pelvic fascia until at least one sharpened or pointed electrode tip, preferably two electrode tips, of the apparatus penetrate a fat layer tissue structure and are in contact with a back surface of the endo-pelvic fascia so as to directly apply energy to heat the endo-pelvic fascia. Depending on the electrode configuration of the apparatus, as discussed in more detail below, treatment may further include releasing the apparatus from the back surface of the endo-pelvic fascia, rotating the apparatus about a center of the cannula within the space of retzius, and re-penetrating the electrode tip from behind the endo-pelvic fascia. Typically, such retrograde protocols are performed twice, with one treatment on each side of the urethra. Treatment may be carried out sequentially with one system or simultaneously with a dual penetrating heating system. After the desired treatment is effected, the apparatus is retracted back inside the cannula and the cannula removed from the vagina. It will be appreciated that the mechanisms of actuation may be manual or automatically driven by a variety of means, such as electro-magnetism, spring loading, power operation, etc.

In another embodiment, treatment further comprises inserting an expansible blade member through the cannula and deploying the blade member so a distal end thereof is expanded in the space of retzius. The blade member mechanically removes a portion of a fat layer tissue structure surrounding a back surface of the endo-pelvic fascia. In particular, the blade member is rotated and pulled in a proximal direction toward the endo-pelvic fascia. The cannula may additionally be pulled back in a proximal direction so as to facilitate removal of the fat layer tissue structure. Once the fat layer surrounding the cannula is removed, the blade member is retracted through the cannula. The expansible electrode apparatus is then inserted through the cannula and deployed so that a distal end thereof is expanded in the space of retzius. The expanded apparatus is then pulled in a proximal direction toward the endo-pelvic fascia until at least one electrode, preferably a pair of electrodes, of the apparatus are in contact with a back surface of the endo-pelvic fascia so as to directly apply energy to heat the endo-pelvic fascia.

As noted above, depending on the electrode configuration of the apparatus, treatment may further include releasing the apparatus from the back surface of the endo-pelvic fascia, rotating the apparatus about a center of the cannula within the space of retzius, and re-engaging the electrode with the back surface of the endo-pelvic fascia. Preferably, such retrograde protocols are performed on each side of the urethra either sequentially or simultaneously. After the desired treatment is effected, the apparatus is retracted back inside the cannula and the cannula removed from the vagina. It will be appreciated that the mechanisms of actuation may be manual or automatically driven by a variety of means, such as electro-magnetism, spring loading, power operation, etc.

Any of the systems described herein may further expand the narrow space of retzius to create a larger working space that may be more easily viewed as well as to reduce any inadvertent damage (e.g., heating, cutting) to non-target tissues. For example, a balloon or post coupled to a distal end of the electrode apparatus, blade member, cannula and/or introducer may aid to move non-target overlying vascular muscle tissues away from the space of retzius. In one embodiment, expanding may comprise inflating a balloon at a distal end of the apparatus to help separate the vascularized muscle tissue away from the fat layer tissue structure and target endo-pelvic fascia. Use of the expansible balloon may also provide for a variable amount of lift or separation as well as may apply force to the electrode apparatus obviating the need for manual pulling in a proximal direction. It will be further appreciated that any of the procedures described herein may be visualized with the aid of an endoscope, camera, or other imaging modalites that are either separated from or incorporated into any component of the incontinence system. For example, an endoscope may be used within the introducer to visualize tissue penetration in order to minimize over insertion and consequent injury to the vascularized muscle tissue overlying the space of retzius.

In another aspect of the present invention, a method for heating support tissue of a patient comprises positioning a cannula within a patient's vagina. A distal end of the cannula is penetrated through the vaginal mucosa, collagenous endo-pelvic fascia, and a fat layer tissue structure. An expansible electrode apparatus is inserted through the cannula and deployed in a space of retzius. Energy is applied to heat the endo-pelvic fascia.

In yet another aspect of the present invention, a method for heating support tissue of a patient comprises applying energy from behind collagenous endo-pelvic fascia to heat the endo-pelvic fascia. Applying may comprise positioning an electrode apparatus in a space of retzius, in a fat layer tissue structure, and/or against a back surface of the endo-pelvic fascia.

In still another aspect of the present invention, a system for heating support tissue of a patient comprises a cannula and an expansible electrode apparatus partially disposed within the cannula. A distal end of the apparatus is deployable at a fixed point behind collagenous endo-pelvic fascia, preferably the space of retzius. The endo-pelvic fascia supports at least a portion of a patient's bladder, urethra, or bladder neck. The expansible electrode apparatus is preferably energized with RF heating power. It will be appreciated that the expansible electrode apparatus may take on a variety of electrode configurations. For example, the expansible electrode apparatus may comprise a single electrode, a plurality of electrodes, or an array of electrodes. Utilization of an array of electrodes allows for treatment around an apparatus perimeter at once while a pair of electrodes may include rotation of the apparatus about the center of the cannula to treat successively around the perimeter. Further, it will be appreciated that the electrode shape, size, and spacing may be varied to control energy penetration and flux. In one embodiment, the apparatus comprises a pair of spring loaded arms, wherein each arm has at least one sharpened electrode tip.

Any of the systems of the present invention may further include an introducer (e.g., scalpel, needle, etc.) to aid in cannula penetration. In addition, the system may include an expansible blade apparatus to facilitate removal of the fat layer tissue structure. An inflatable balloon or post having a soft tip may be coupled to or integrally formed with a distal end of the expansible electrode apparatus, blade member, introducer, and/or cannula to provide an enhanced working space. Further, an endoscope, camera, or other imaging modalites may also be included for use with the expansible electrode apparatus, blade member, introducer, and/or cannula for visualization purposes.

A further understanding of the nature and advantages of the present invention will become apparent by reference to the remaining portions of the specification and drawings.

BRIEF DESCRIPTION OF THE DRAWINGS

The following drawings should be read with reference to the detailed description. Like numbers in different drawings refer to like elements. The drawings, which are not necessarily to scale, illustratively depict embodiments of the present invention and are not intended to limit the scope of the invention.

FIGS. 6A through 6H illustrate a least invasive method for accessing and treating the endo-pelvic fascia with a cannula/expansible electrode assembly constructed in accordance with the principles of the present invention.

DETAILED DESCRIPTION OF THE INVENTION

Figure 1A:
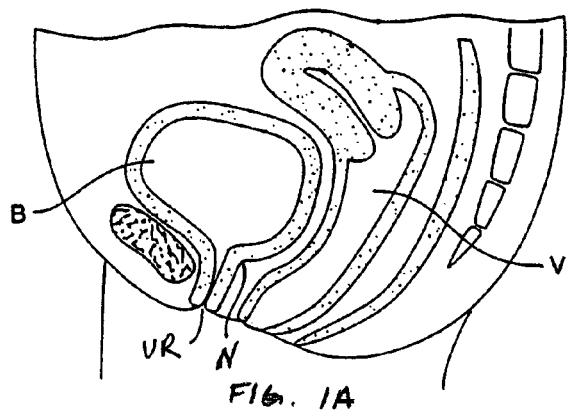
FIGS. 1A and 1B illustrate cross-sectional views showing the urinary bladder, urethra, bladder neck, pelvic tissue support structures, and vaginal cavity.
Figure 1B:
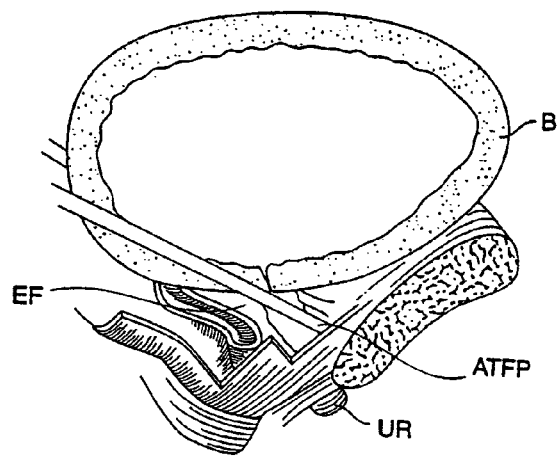

FIG. 1A illustrates a cross-sectional view showing the urinary bladder B, urethra UR, bladder neck N, and vaginal cavity V. Pelvic tissue support structures which generally maintain the position of the urinary bladder B, urethra UR, and bladder neck N are illustrated in FIG. 1B. The endo-pelvic fascia EF defines a hammock-like structure which extends between the arcus tendineus fascia pelvis ATFP. These latter structures extend substantially between the anterior and posterior portions of the pelvis so that the endo-pelvic fascia EF largely defines the pelvic floor.

Figure 2:
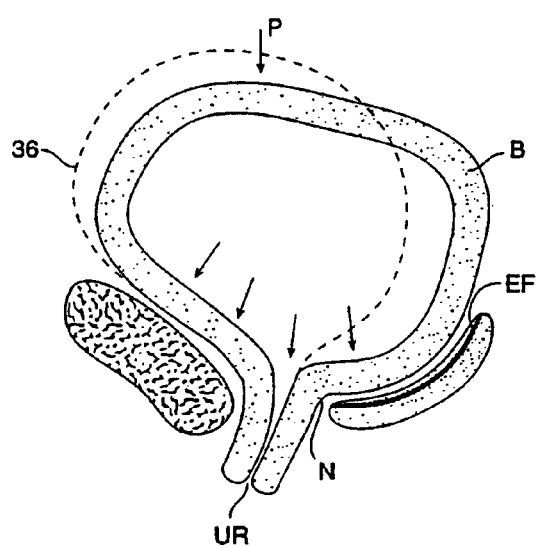
FIG. 2 illustrates a cross-sectional view of a patient suffering from urinary stress incontinence due to inelastic stretching of the endo-pelvic fascia.

Referring now to FIG. 2, a cross-sectional view of a patient suffering from urinary stress incontinence due to inelastic stretching of the endo-pelvic fascia is illustrated. In particular, bladder B can be seen to have dropped from its nominal position, as shown in phantom by outline 36. While endo-pelvic fascia EF still supports bladder B to maintain continence when the patient is at rest, a momentary pulse P opens the bladder neck N resulting in a release through urethra UR.

Figure 3:
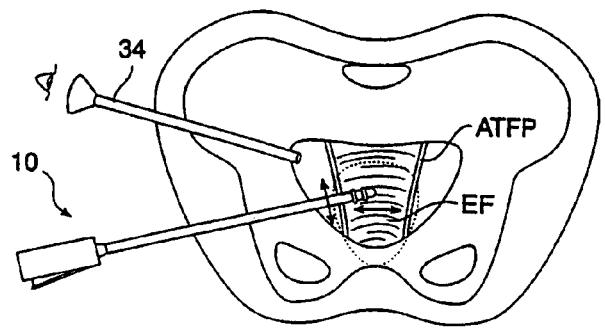
FIG. 3 illustrates a simplified cross-sectional view of the pelvis showing the endo-pelvic fascia and arcus tendineus fascia pelvis and a method for treating urinary stress incontinence by sweeping a probe directly across the endo-pelvic fascia from an anterior approach to reposition and/or raise the urinary bladder.

Referring now to FIG. 3, a simplified cross-sectional view of the pelvis showing the endo-pelvic fascia EF and arcus tendineus fascia pelvis ATFP is illustrated. Further illustrated is a method for treating urinary stress incontinence by sweeping a probe 10 directly across the endo-pelvic fascia EF from an anterior approach, as described in more detail in U.S. Pat. No. 6,091,995. This therapy for treating incontinence applies gentle heating to shrink the length of the support tissues and return bladder B to its nominal position. Advantageously, the bladder is still supported by the fascia, muscles, ligaments, and tendons of the original pelvic support tissues. Using gentle resistive heating between bipolar electrodes, the endo-pelvic fascia EF and arcus tendineus fascia pelvis ATFP are controllably contracted to shrink them and re-elevate the bladder towards its original position.

Access to and direction of the therapy, as schematically illustrated in FIG. 3, will often be provided by a surgical incision directly into a vaginal wall and mucosa of a patient. Abdominal puncture sites are created so as to provide for direct treatment of the endo-pelvic fascia EF from the anterior approach of the endo-pelvic fascia. A laparoscope 34 is also shown to direct optical imaging, often while the pelvic region is distended using gas insufflation. Tissue contraction with probe 10 will generally be performed in at least one of two modes: spot treatments and line treatments. Advantageously, repeatedly sweeping probe 10 across adjacent areas of the endo-pelvic fascia can raise the bladder in discrete increments.

Figure 4:
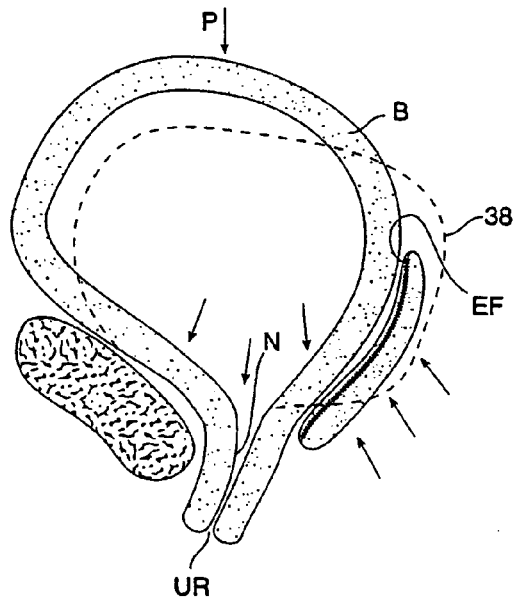
FIG. 4 illustrates an improved bladder support provided by selectively shrinking and/or stiffening the endo-pelvic fascia as a therapy for urinary stress incontinence.

As shown in FIG. 4, by selectively contracting the natural pelvic support tissues, bladder B can be elevated from its lowered position as shown by lowered outline 38. A pressure pulse P is resisted in part by endo-pelvic fascia EF, which supports the lower portion of the bladder and helps maintain the bladder neck in a closed configuration. Hence, fine-tuning of the support provided by the endo-pelvic fascia is possible through selective contraction of the endo-pelvic fascia EF to close the bladder neck N and raise bladder B upward.

Figure 5:
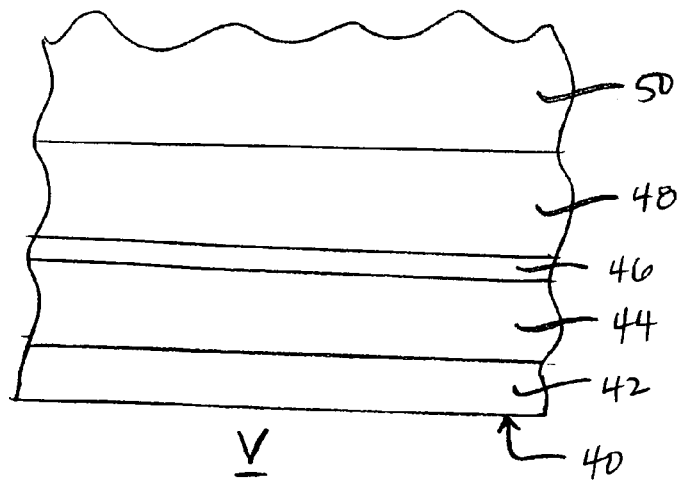
FIG. 5 illustrates a cross-sectional view of the vaginal cavity, vaginal mucosa, endo-pelvic fascia, fat layer tissue structure, space of retzius, and vacularized muscle tissue.

Referring now to FIG. 5, a cross-sectional view in a northerly direction from the vaginal cavity V is illustrated. In particular, vaginal mucosa 42 is shown overlying the vaginal wall 40. Endo-pelvic fascia 44 is shown overlying the vaginal mucosa. A fat tissue structure 46 providing a thin insulating layer is shown overlying the endo-pelvic support tissue 44. A thin narrow space, known as the space of retzius 48, is provided between the fat tissue layer 44 and vascularized muscle tissue 50 and behind the endo-pelvic fascia 44.

Figure 6A:
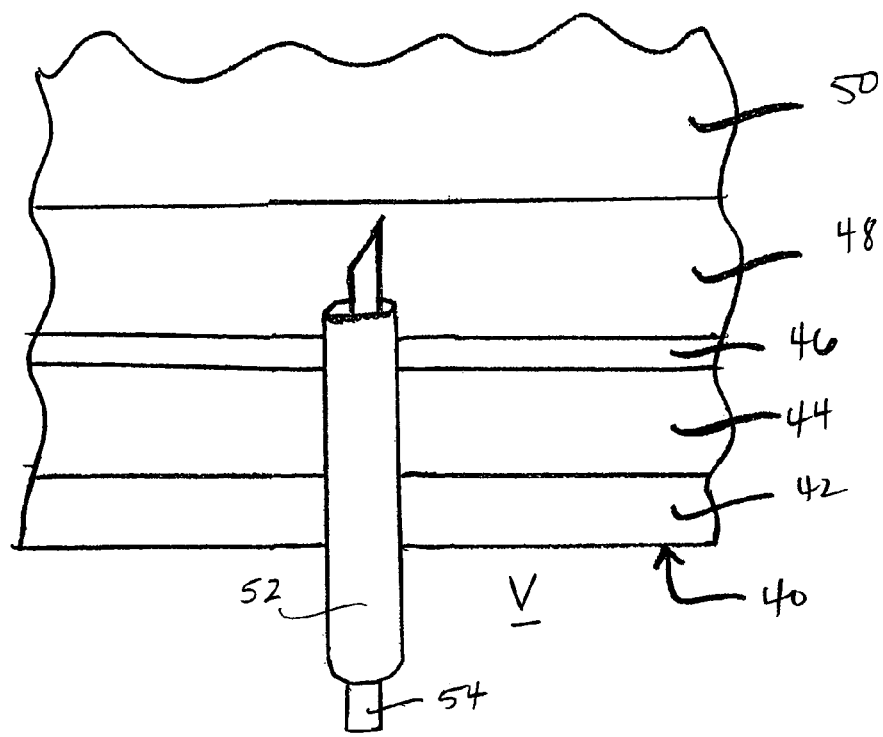

Referring now to FIGS. 6A through 6H, an exemplary least invasive method for accessing and treating the endo-pelvic fascia from a posterior approach is illustrated. A cannula 52 or sheath in conjunction with an introducer 54 (e.g., scalpel, needle, etc.) is positioned within a patient's vaginal cavity V, as shown in FIG. 6A. A distal end of the cannula 52 is penetrated through the vaginal mucosa 42, collagenous endo-pelvic fascia 44, and a fat layer tissue structure 46. In particular, penetrating may comprise advancing the pointed introducer 54 behind the collagenous endo-pelvic fascia 44, sliding the cannula 52 over the introducer 54, and removing the introducer 54 while the distal end of the cannula 52 is left in place behind the endo-pelvic fascia 44. Preferably, the cannula 52 is positioned in the space of retzius 48, as shown in FIG. 6A, or in the fat layer tissue structure 46 surrounding a back surface of the endo-pelvic fascia 44.

The cannula 52 is left embedded in the tissue for the remainder of the procedure. The cannula 52 may be formed from a variety of medical grade materials including polymer materials (e.g., nylon, polyurethane, polyimide), metal materials (e.g., stainless steel, NITINOL®), plastic materials, and combinations thereof. The cannula will have a tubular shape and dimensions that can accommodate insertion of the various components of the incontinence system, including the introducer 54, expandable energy applying applicator, expansible blade member, etc.

The penetrating cannula 52 advantageously allows for proper navigation and application of the heating apparatus from behind the endo-pelvic fascia 44, particularly in tissue planes that are difficult to access. For example, cannula penetration may facilitate access to the desired areas in women with small anatomical structures. Additionally, cannula penetration provides a non-surgical incisionless treatment which obviates the need for abdominal puncture sites or stitches to the vaginal wall 40 or mucosa 42. It will further be appreciated that such non-surgical treatments do not implement any cooling modalities, thereby simplifying fabrication and use of such incontinence systems. It will be appreciated that the above depictions are for illustrative purposes only and do not necessarily reflect the actual shape, size, or dimensions of the incontinence system. This applies to all depictions hereinafter.

Figure 6B:
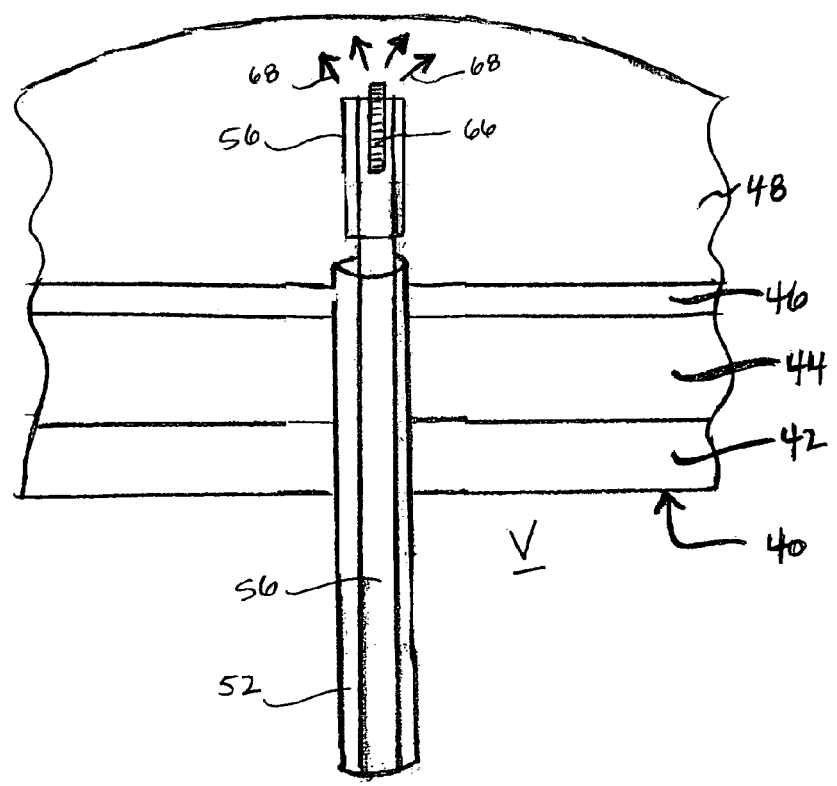

Referring now to FIGS. 6B and 6C, treatment further comprises inserting an expansible blade member 56 through the cannula 52 and deploying the blade member 56 so that a distal end thereof is expanded in the space of retzius 48. The blade member 56 mechanically removes or "shaves" a portion of the fat layer tissue structure 46 surrounding a back surface 62 of the endo-pelvic fascia 44, as best seen in FIG. 6D. In particular, the blade member 56 is rotated, as depicted by arrow 58, and pulled in a proximal direction, as depicted by arrow 60, toward the endo-pelvic fascia 44. The cannula 52 may additionally be pulled back in a proximal direction so as to facilitate removal of the fat layer tissue structure 46. Once the fat layer 46 surrounding the cannula 52 is cleared away by the shaving action, the blade member 56 is retracted through the cannula 52. It will be appreciated that removal of the fat layer structure 46 is not necessary for the application of energy from behind the endo-pelvic fascia. For example, the energy applying applicator may project microwave energy from the space of retzius 48 directly through the fat layer tissue structure 46 and into the back surface 62 of the target endo-pelvic tissue 44. Still further, the energy applying element may be penetrated in a reverse direction through the fat layer tissue structure 46 and into the back surface 62 of the target endo-pelvic tissue 44 as discussed in more detail with respect to the FIG. 7.

Referring now to FIG. 6E, a top view of the blade member 56 in an expanded configuration is illustrated. The blade member 56 comprises a plurality of shaving arms 64. It will be appreciated however that the expansible blade member 56 may take on a variety of other configurations depending on the treatment site and access approach, such as a single blade, non-circular shaped blade, sliding blade, etc. The blade member 56 may be formed from a variety of medical grade materials, including metal materials (e.g., stainless steel, NITINOL®), polymer materials (e.g., nylon, polyurethane, polyimide), plastic materials, and combinations thereof. The blade member 56 in a retracted configuration will have a diameter that is smaller than an inner diameter of the cannula 52, as shown in FIG. 6B. The blade member 56 in the expanded configuration will have a diameter in a range from about 15 mm to about 25 mm, preferably in a range from about 19 mm to about 22 mm.

Referring back to FIGS. 6B and 6C, an endoscope 66 may also be included for use with any components of the incontinence system for visualization purposes. In this illustration, the endoscope 66 is shown coupled to the blade member 56 for viewing the ceiling of the pelvic cavity prior to deployment, as depicted by arrows 68, and the top surface of the fat layer tissue structure 46 prior to tissue dissection, as depicted by arrows 70. Any of the present method steps disclosed herein may be optically directed using a variety of existing endoscopic structures, depending on the treatment site and access approach. Laparoscopes, arthroscopes, hysteroscopes, or the like may also be used (or adapted for use) in the present methods. Alternatively, conventional optical imaging capabilities (e.g., camera) or specialized fiber optic image guides may be used, either separated from or incorporated into any component of the incontinence system. Still further, therapy may be directed using a remote imaging modality, such as fluoroscopy, ultrasound, magnetic resonance imaging, or the like.

Figure 6F:
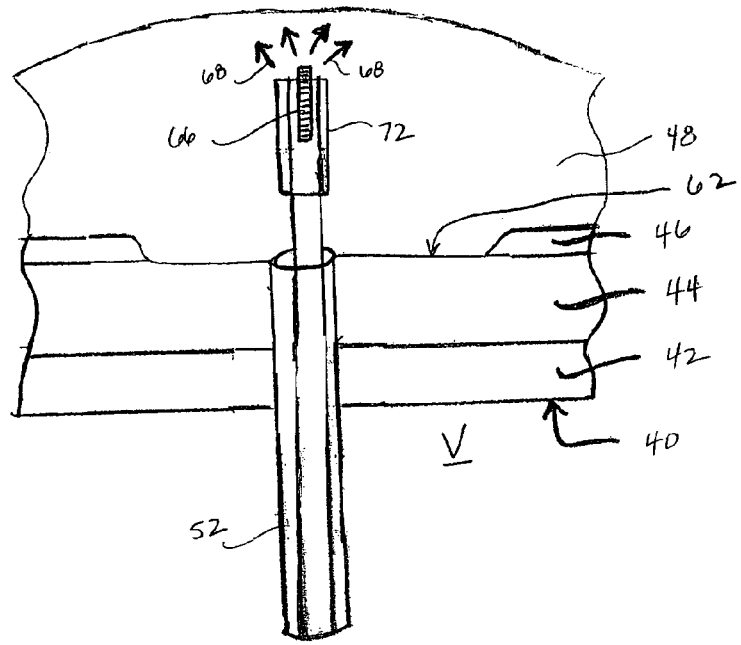

Referring now to FIG. 6F, the expansible electrode apparatus 72 is then inserted through the cannula 52 after the fat layer 46 is cleared. The expansible electrode apparatus 72 is deployed so that a distal end thereof is expanded in the space of retzius 48. As shown in FIG. 6G, the expanded apparatus 72 is then pulled in a proximal direction, as depicted by arrow 74, towards the endo-pelvic fascia 44 until electrodes 76 of the apparatus 72 are in contact with the back surface 62 of the endo-pelvic fascia 44. Energy is then applied through the electrodes 76 to heat the endo-pelvic fascia 44 according to a desired algorithm from this posterior approach. The desired heating algorithm may take into account a variety of factors including a thickness of the endo-pelvic fascia, which may easily be measured when the fascia is penetrated. An endoscope 66 is also inserted with the apparatus 72 to facilitate proper insertion by viewing an upward direction, as denoted by arrows 68, at the overlying muscular tissue 50. Proper deployment and application of the apparatus 72 may also be facilitated by the endoscope 66 viewing a downward direction at the back surface 62 of the endo-pelvic fascia 44.

Advantageously, treatment from this posterior approach provides for simple and reliable placement and application of the apparatus 72 which in turn enhances both safety and efficacy of such retrograde methodologies. Heating the endo-pelvic fascia 44 treats conditions such as urinary stress incontinence and bladder neck descent by shrinking, stiffening, and/or bulk and buttressing the tissue structure 44 to increase support of the urethra UR and bladder B. The endo-pelvic fascia 44 may be heated to a desired temperature in a range from about 50° C. to about 80° C., preferably in a range from about 55° C. to about 75° C. and for a duration of time in a range from about 100 seconds to about 500 seconds, preferably in a range from about 150 seconds to about 300 seconds.

It will be appreciated that there are a number of energy modalities to heat, shrink, stiffen and/or buttress the endo-pelvic fascia 44 which supports at least a portion of patient's bladder, urethra, or bladder neck. Preferably, radio frequency (RF) power is used to project energy into the endo-pelvic fascia via bipolar electrodes 76. It will be appreciated however that the energy source may be configured for both bipolar and monopolar transmission. Bipolar instruments are typically connected to both poles of an energy source, wherein the energy flow is typically limited to the working end of the bipolar instrument (e.g., distal end of severing element). Monopolar devices are typically used in conjunction with a grounding pad wherein one pole of the energy source is coupled to the instrument and the other pole is coupled to the grounding pad. The energy flow in monopolar devices travels from the instrument (e.g., severing element) to the grounding pad. Still further, the applied energy may comprise microwave energy, ultrasound energy, laser energy, passive-resistive heating, infrared, or the like.

Depending on the electrode 76 configuration of the apparatus 72, treatment may further include releasing the apparatus 72 from the back surface 62 of the endo-pelvic fascia 44, rotating the apparatus 72 about a center of the cannula 52 within the space of retzius 48 as denoted by arrow 78, and re-engaging the electrode 76 with the back surface 62 of the endo-pelvic fascia 44. Typically, such retrograde protocols are performed twice, with one treatment on each side of the urethra UR. Treatment may be carried out sequentially with one penetrating heating system or simultaneously with a dual penetrating heating system. After the desired treatment is effected, the apparatus 72 is retracted back inside the cannula 52 and the cannula 52 removed from the vaginal cavity V.

Figure 6H:
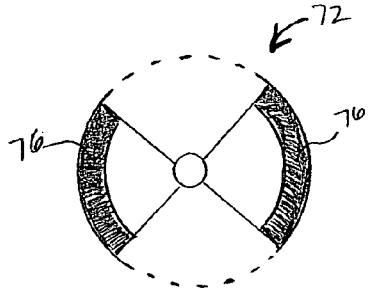
Figure 6G:
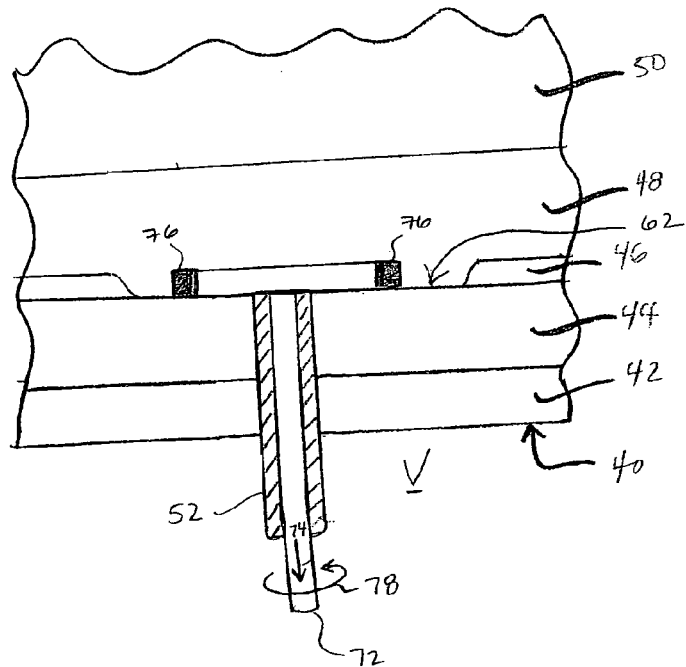

Referring now to FIG. 6H, a top view of the energy applying apparatus 72 in an expanded configuration is illustrated. It will be appreciated that the energy applying apparatus 72 may take on a variety of configurations depending on the treatment site, access approach, and/or energy modality. For example, the energy applying elements may take on any of the forms described in U.S. Pat. Nos. 6,091,995; 6,216,704; 6,558,381; 6,546,934; 6,156,060; 6,572,639; 6,776,779; and 6,292,700 and U.S. patent application Ser. No. 10/759,732. In this illustration, the energy applying element 72 comprises a pair of separated bipolar, curved electrodes 76. Further, it will be appreciated that the electrode 76 shape, size, and spacing may be designed to control energy penetration and flux. The apparatus 72 in a retracted configuration will have a diameter that is smaller than the inner diameter of the cannula 52, as shown in FIG. 6F. The apparatus 72 in the expanded configuration may define a perimeter diameter, as shown by the dotted line in FIG. 6H, in a range from about 15 mm to about 25 mm, preferably in a range from about 19 mm to about 22 mm.

Figure 7:
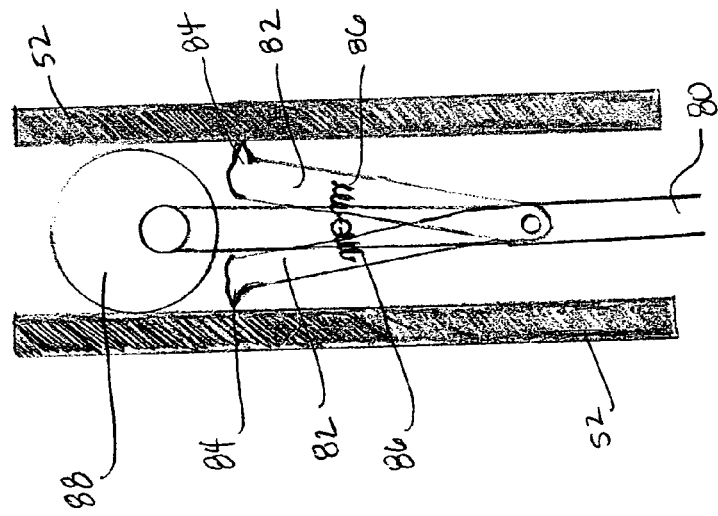
FIG. 7 illustrates another embodiment of the cannula/expansible electrode assembly constructed in accordance with the principles of the present invention.

Referring now to FIG. 7, another embodiment of the expansible energy applying apparatus 80 in a retracted configuration is illustrated. In particular, the apparatus 80 comprises a pair of spring loaded arms 82, wherein each arm 82 has at least one sharpened or pointed electrode tip 84. Significantly, the electrode tip 84 allows for heating from behind the endo-pelvic fascia 44 without removal of the fat tissue layer 46, as discussed in more detail below. The springs or coils 86 may be formed from a variety of medical grade materials, including stainless steel, shape memory alloy, superelastic metal, and the like. The arms 82 may also be formed from medical grade materials including polymer materials (e.g., nylon, polyurethane, polyimide), metal materials (e.g., stainless steel, NITINOL®), plastic materials, and combinations thereof. The apparatus 80 in a retracted configuration will have a dimension that is smaller than the inner diameter of the cannula 52. The apparatus 80 in the expanded configuration may define a perimeter length in a range from about 15 mm to about 25 mm, preferably in a range from about 19 mm to about 22 mm.

A post 88 having a soft tip may also be integrally formed with a distal end of the expansible electrode apparatus 80 to expand the narrow space of retzius 48. This in turn creates a larger working space that may be more easily viewed (by an endoscope 66) as well as may reduce any inadvertent damage (e.g., heating) to non-target tissues 50. The post 88 may take on a variety of other configurations depending on the treatment site and access approach, such as expansible balloon as discussed above. The post 88 may be formed from a variety of medical grade materials, including polymer materials (e.g., nylon, polyurethane, polyimide), metal materials (e.g., stainless steel, NITINOL®), plastic materials, and combinations thereof. Generally, the post 88 will have a diameter in a range from about 15 mm to about 25 mm, preferably in a range from about 19 mm to about 22 mm.

Figure 8A:
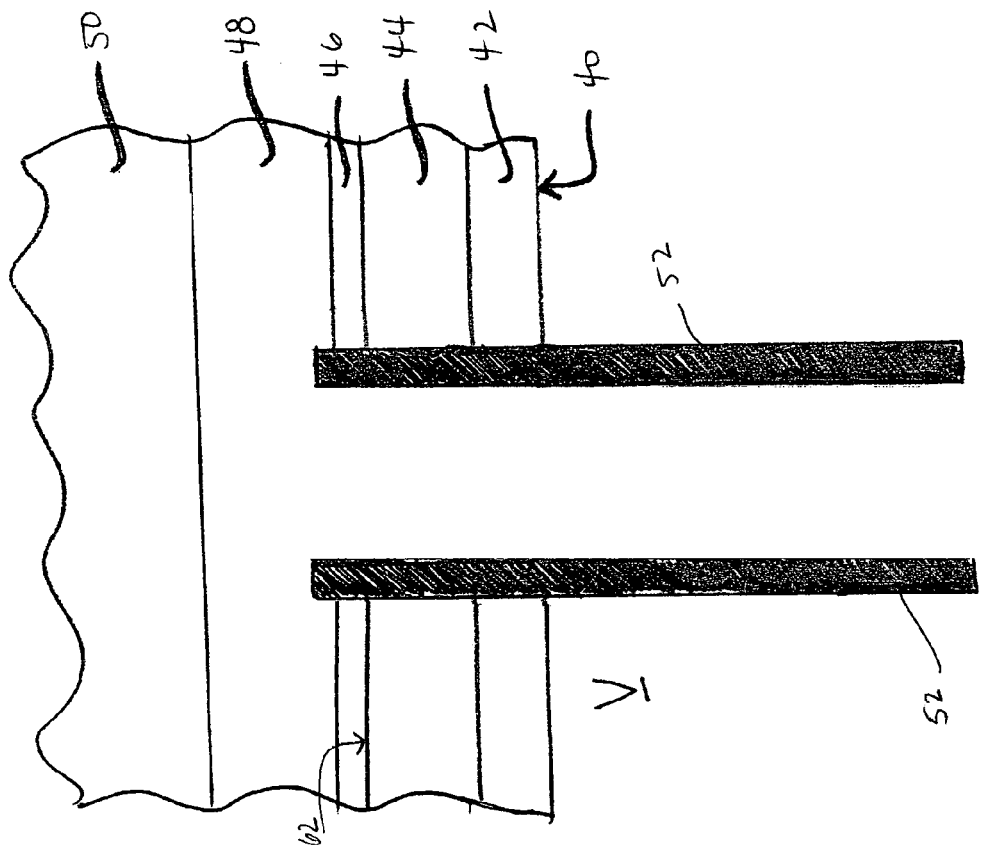
FIGS. 8A through 8C illustrate another least invasive method for accessing and treating the endo-pelvic fascia employing the assembly of FIG. 7 according to the principles of the present invention.
Figure 8C:
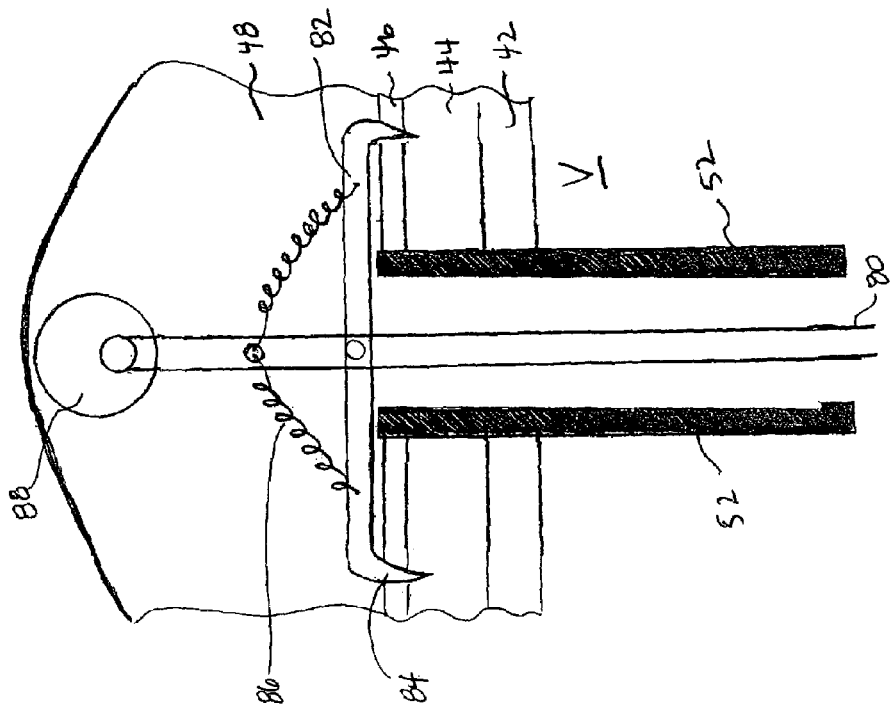
Figure 8B:
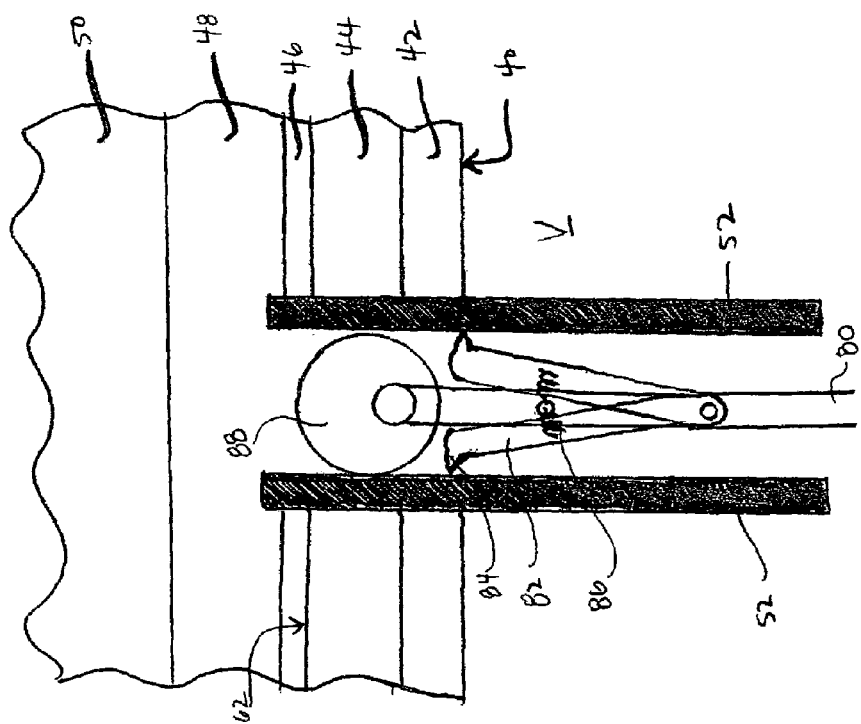

Referring now to FIGS. 8A through 8C, another least invasive method for accessing and treating the endo-pelvic fascia from a posterior approach employing the assembly of FIG. 7 is illustrated. As shown in FIG. 8A, the cannula 52 is penetrated through the vaginal mucosa 42, endo-pelvic fascia 44, and fat tissue layer 46, until a distal end enters the space of retzius 48. Once the cannula 52 is in place, the expansible electrode apparatus 80 is inserted through the cannula 52 until a distal end of the apparatus 80 is deployed in the space of retzius 48, as shown in FIGS. 8B and 8C. In particular, the springs 86 allow for expansion of the arms 82 when the apparatus 80 is released from the constraining cannula 52. At the same time, the post 88 may help separate the vascularized muscle tissue 50 away from the fat layer tissue structure 46 and target endo-pelvic fascia 44 so as to expand the space of retzius 48.

Once the apparatus 80 is in the expanded configuration, the apparatus 80 is pulled in a proximal direction toward the endo-pelvic fascia 44 until the shallow electrode tips 84 penetrate a fat layer tissue structure 46 and are in contact with the back surface 62 of the endo-pelvic fascia 44. The electrode tips 84 then directly apply energy to the back surface 62 of the endo-pelvic fascia 44 to obtain the desired heating from this posterior approach. The desired heating algorithm may take into account a variety of factors including a thickness of the endo-pelvic fascia, which may easily be measured when the fascia is penetrated. Treatment may further include releasing the apparatus 80 from the back surface 62 of the endo-pelvic fascia 44, rotating the apparatus 80 about a center of the cannula 52 within the space of retzius 48, and re-penetrating the electrode tips 84 from behind the endo-pelvic fascia 44. After the desired treatment is effected, the apparatus 80 is retracted back inside the cannula 52 and the cannula 52 removed from the vaginal cavity V.

Figure 9:
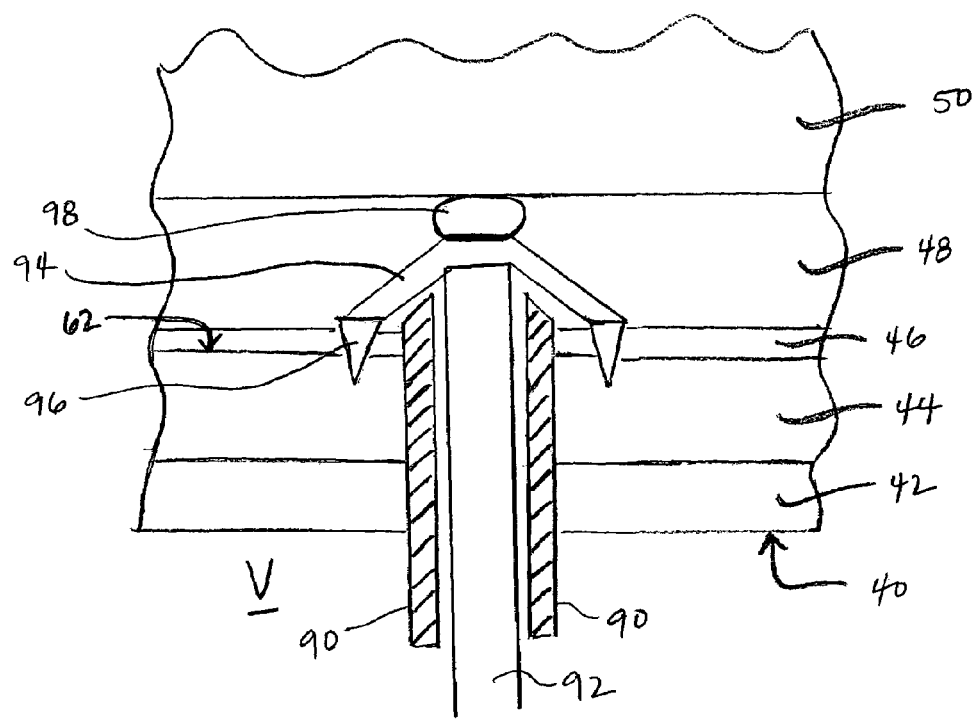
FIG. 9 illustrates yet another embodiment of a trocar/expansible electrode assembly constructed in accordance with the principles of the present invention for accessing and treating the endo-pelvic fascia.

Referring now to FIG. 9, another incontinence system of the present invention is illustrated. The system of FIG. 9 includes a sharpened trocar 90 in lieu of the cannula 52/introducer 54 assembly for penetration behind the endo-pelvic fascia 44 and into the space of retzius 48. The trocar 90 may comprise a separate component of the system or alternatively form a partially integrated system with the expansible electrode assembly 92. The expansible electrode assembly 92 includes flexible arms 94 that are inserted through the trocar 90 and expand into the space of retzius 48 once released from the constraining trocar 90. The apparatus 92 is then pulled in a proximal direction toward the endo-pelvic fascia 44 until the shallow electrode tips 96 penetrate the fat layer tissue structure 46 and are in contact with the back surface 62 of the endo-pelvic fascia 44. Energy is then applied through the electrode tips 96 to heat the endo-pelvic fascia 44 according to an appropriate algorithm from this posterior approach. After the desired treatment is effected, the apparatus 92 is retracted back inside the trocar 90 and the trocar 90 removed from the vaginal cavity V. In this embodiment, an expansible balloon 98 coupled to a distal end of the apparatus 92 further aids in smoothness of operation of the apparatus 92, particularly during its removal.

Although certain exemplary embodiments and methods have been described in some detail, for clarity of understanding and by way of example, it will be apparent from the foregoing disclosure to those skilled in the art that variations, modifications, changes, and adaptations of such embodiments and methods may be made without departing from the true spirit and scope of the invention. Therefore, the above description should not be taken as limiting the scope of the invention which is defined by the appended claims.

What is claimed is:

1. A method for heating support tissue of a patient comprising:
   providing an expansible electrode apparatus partially disposed within a cannula;
   penetrating a distal end of the cannula through collagenous endo-pelvic fascia and behind the endo-pelvic fascia;
   deploying a distal end of the expansible electrode apparatus at a fixed point behind the collagenous endo-pelvic fascia; and
   applying energy to heat the endo-pelvic fascia.

2. A method as in claim 1, wherein the fixed point behind collagenous endo-pelvic fascia comprises a space of retzius.

3. A method as in claim 1, wherein heating the endo-pelvic fascia treats urinary stress incontinence.

4. A method as in claim 1, wherein heating the endo-pelvic fascia corrects bladder neck descent.

5. A method as in claim 1, wherein heating shrinks the endo-pelvic fascia.

6. A method as in claim 1, wherein heating stiffens the endo-pelvic fascia.

7. A method as in claim 1, wherein the applied energy comprises RE energy.

8. A method as in claim 1, wherein the applied energy is selected from one of the group comprising microwave energy, ultrasound energy, laser energy, passive-resistive heating, or infrared.

9. A method as in claim 1, further comprising positioning the cannula within a patient's vagina.

10. A method as in claim 9, wherein penetrating comprises advancing the cannula through vaginal mucosa, endo-pelvic fascia, and a fat layer tissue structure.

11. A method as in claim 9, wherein penetrating comprises advancing an introducer through the collagenous endo-pelvic fascia, sliding the cannula over the introducer, and removing the introducer while the cannula is positioned behind the endo-pelvic fascia.

12. A method as in claim 9, wherein penetrating comprises positioning the cannula in a space of retzius.

13. A method as in claim 9, wherein penetrating comprises positioning the cannula in a fat layer tissue structure surrounding a back surface of the endo-pelvic fascia.

14. A method as in claim 9, wherein deploying comprises inserting the expansible electrode apparatus through the cannula until a distal end of the apparatus is expanded in a space of retzius.

15. A method as in claim 14, further comprising pulling the expanded apparatus in a proximal direction toward the endo-pelvic fascia until at least one sharpened electrode tip of the apparatus penetrates a fat layer tissue structure and is in contact with a back surface of the endo-pelvic fascia so as to directly apply energy to heat the endo-pelvic fascia.

16. A method as in claim 15, further comprising rotating the apparatus about a center of the cannula.

17. A method as in claim 16, further comprising retracting the apparatus back inside the cannula and removing the cannula from the vagina.

18. A method as in claim 9, further comprising inserting an expansible blade member through the cannula and deploying the member so a distal end thereof is expanded in a space of retzius.

19. A method as in claim 18, further comprising mechanically removing a portion of a fat layer tissue structure surrounding a back surface of the endo-pelvic fascia by rotating and pulling the member in a proximal direction toward the endo-pelvic fascia.

20. A method as in claim 19, further comprising retracting the blade member through the cannula.

21. A method as in claim 20, further comprising inserting the expansible electrode apparatus through the cannula and then deploying the apparatus so that a distal end thereof is expanded in the space of retzius.

22. A method as in claim 21, further comprising pulling the expanded apparatus in a proximal direction toward the endo-pelvic fascia until an electrode of the apparatus is in contact with the back surface of the endo-pelvic fascia so as to directly apply energy to heat the endo-pelvic fascia.

23. A method as in claim 22, further comprising rotating the apparatus about a center of the cannula.

24. A method as in claim 23, further comprising retracting the apparatus back inside the cannula and removing the cannula from the vagina.

25. A method as in claim 1, further comprising expanding a space of retzius.

26. A method as in claim 25, wherein expanding comprises inflating a balloon at a distal end of the apparatus.

27. A method as in claim 1, further comprising visualizing anyone of the method steps.

28. A method for heating support tissue of a patient comprising:
   positioning a cannula within a patient's vagina;
   penetrating a distal end of the cannula through the vaginal mucosa, collagenous endo-pelvic fascia, and a fat layer tissue structure;
   inserting an expansible electrode apparatus through the cannula;
   deploying the expansible electrode apparatus in a space of retzius; and
   applying energy to heat the endo-pelvic fascia.

29. A method for heating support tissue of a patient comprising:
   applying energy from behind collagenous endo-pelvic fascia to heat the endo-pelvic fascia.

30. A method as in claim 29, wherein applying comprises positioning an electrode apparatus in a space of retzius.

31. A method as in claim 29, wherein applying comprises positioning an electrode apparatus against a back surface of the endo-pelvic fascia.

32. A system for heating support tissue of a patient comprising:
   a cannula;
   an expansible electrode apparatus partially disposed within the cannula and having at least one electrode, wherein a distal end of the apparatus is deployable at a fixed point behind collagenous endo-pelvic fascia; and
   a post having a soft tip extending from the distal end of the expansible electrode apparatus;
   wherein the expansible electrode apparatus comprises at least one sharpened electrode tip.

33. A system as in claim 32, wherein the fixed point behind collagenous endo-pelvic fascia comprises a space of retzius.

34. A system as in claim 32, wherein -the endo-pelvic fascia supports at least a portion of the patient's bladder, urethra, or bladder neck.

35. A system as in claim 32, wherein the expansible electrode apparatus is energized with RF power.

36. A system as in claim 32, wherein the expansible electrode apparatus comprises a plurality of electrodes.

37. A system as in claim 32, wherein the expansible electrode apparatus comprises an array of electrodes.

38. A system as in claim 32, wherein the expansible electrode apparatus comprises a pair of spring loaded arms.

39. A system as in claim 32, further comprising an introducer.

40. A system as in claim 32, further comprising an expansible blade apparatus.

41. A system as in claim 32, further comprising an endoscope.

42. A method for heating support tissue of a patient comprising:
deploying an expansible electrode apparatus at a fixed point behind collagenous endo-pelvic fascia, wherein the fixed point behind collagenous endo-pelvic fascia comprises a space of retzius; and
applying energy to heat the endo-pelvic fascia.

43. A method for heating support tissue of a patient comprising:
positioning a cannula within a patient's vagina;
penetrating a distal end of the cannula through collagenous endo-pelvic fascia and behind the endo-pelvic fascia, wherein penetrating comprises positioning the cannula in a space of retzius;
deploying an expansible electrode apparatus at a fixed point behind the collagenous endo-pelvic fascia; and
applying energy to heat the endo-pelvic fascia.

44. A method for heating support tissue of a patient comprising:
positioning a cannula within a patient's vagina;
penetrating a distal end of the cannula through collagenous endo-pelvic fascia and behind the endo-pelvic fascia, wherein penetrating comprises positioning the cannula in a fat layer tissue structure surrounding a back surface of the endo-pelvic fascia;
deploying an expansible electrode apparatus at a fixed point behind the collagenous endo-pelvic fascia; and
applying energy to heat the endo-pelvic fascia.

45. A method for heating support tissue of a patient comprising:
positioning a cannula within a patient's vagina;
penetrating a distal end of the cannula through collagenous endo-pelvic fascia and behind the endo-pelvic fascia;
deploying an expansible electrode apparatus at a fixed point behind the collagenous endo-pelvic fascia, wherein deploying comprises inserting the expansible electrode apparatus through the cannula until a distal end of the apparatus is expanded in a space of retzius; and
applying energy to heat the endo-pelvic fascia.

46. A method for heating support tissue of a patient comprising:
positioning a cannula within a patient's vagina;
penetrating a distal end of the cannula through collagenous endo-pelvic fascia and behind the endo-pelvic fascia;
inserting an expansible blade member through the cannula and deploying the member so a distal end thereof is expanded in a space of retzius;
deploying an expansible electrode apparatus at a fixed point behind the collagenous endo-pelvic fascia; and
applying energy to heat the endo-pelvic fascia.

47. A method for heating support tissue of a patient comprising:
deploying an expansible electrode apparatus at a fixed point behind collagenous endo-pelvic fascia;
expanding a space of retzius; and
applying energy to heat the endo-pelvic fascia.

48. A system for heating support tissue of a patient comprising:
a cannula;
an expansible electrode apparatus partially disposed within the cannula and having at least one electrode, wherein a distal end of the apparatus is deployable at a fixed point behind collagenous endo-pelvic fascia, and wherein the expansible electrode apparatus comprises a pair of spring loaded arms; and
a post having a soft tip extending from the distal end of the expansible electrode apparatus.

49. A system for heating support tissue of a patient comprising:
a cannula;
an expansible electrode apparatus partially disposed within the cannula and having at least one electrode, wherein a distal end of the apparatus is deployable at a fixed point behind collagenous endo-pelvic fascia;
a post having a soft tip extending from the distal end of the expansible electrode apparatus; and
an expansible blade apparatus.

* * * * *

UNITED STATES PATENT AND TRADEMARK OFFICE
CERTIFICATE OF CORRECTION

PATENT NO. : 7,536,225 B2  
APPLICATION NO. : 11/040815  
DATED : May 19, 2009  
INVENTOR(S) : Terry E. Spraker Page 1 of 1

It is certified that error appears in the above-identified patent and that said Letters Patent is hereby corrected as shown below:

Claim 7, column 11, line 23, replace "RE" with --RF--

Claim 34, column 12, line 57, replace "wherein -the" with --wherein the--

Signed and Sealed this

Eighteenth Day of August, 2009

David J. Kappos  
*Director of the United States Patent and Trademark Office*